(12) United States Patent
Yoshinaga et al.

(10) Patent No.: US 7,517,981 B2
(45) Date of Patent: Apr. 14, 2009

(54) EFFICIENT PRODUCTION METHOD OF ASCOPYRONE P

(75) Inventors: Kazuhiro Yoshinaga, Kagoshima (JP); Chinami Kawano, Kagoshima (JP)

(73) Assignee: Nihon Starch Co., Ltd., Kagoshima (JP)

( * ) Notice: Subject to any disclaimer, the term of this patent is extended or adjusted under 35 U.S.C. 154(b) by 0 days.

(21) Appl. No.: 10/579,978

(22) PCT Filed: Nov. 18, 2004

(86) PCT No.: PCT/JP2004/017513

§ 371 (c)(1),
(2), (4) Date: May 22, 2006

(87) PCT Pub. No.: WO2005/049599

PCT Pub. Date: Jun. 2, 2005

(65) Prior Publication Data

US 2007/0077618 A1 Apr. 5, 2007

(30) Foreign Application Priority Data

Nov. 20, 2003 (JP) ............................. 2003-391132

(51) Int. Cl.
*C07H 1/00* (2006.01)
*C07H 3/08* (2006.01)
(52) U.S. Cl. ........................................ 536/124; 514/23
(58) Field of Classification Search ................ 536/124; 514/23
See application file for complete search history.

(56) References Cited

U.S. PATENT DOCUMENTS

2003/0203963 A1 10/2003 Elsser et al.

FOREIGN PATENT DOCUMENTS

| JP | 9-505988 | 6/1997 |
|---|---|---|
| JP | 2001-89377 | 4/2001 |
| JP | 2002-27945 | 1/2002 |
| WO | 00/56838 | 9/2000 |
| WO | 02/26060 | 4/2002 |
| WO | 02/26061 | 4/2002 |
| WO | WO 02/26060 A1 * | 4/2002 |
| WO | 03/038084 | 5/2003 |
| WO | 03/038085 | 5/2003 |
| WO | 03/038107 | 5/2003 |

OTHER PUBLICATIONS

Ahmad ("Studies on the Degradation of Some Pentoses and of 1,5-Anhydro-D-Fructose, The Product of the Starch-Degrading Enzyme a-1,4-Glucan Lyase" Phd Thesis, The Swedish University of Agricultural Sciences, Sweden, pp. 1-34, 1995).*

Fred Shafizadeh et al., "1,5-Anhydro-4-Deoxy-D-glycero-Hex-1-en-3-Ulose and Other Pyrolysis Products of Cellulose", Carbohydrate Research 67, pp. 433-447, 1978.

Marie-Antionette Baute et al., "Enzymic Activity Degrading 1,4-α-D-Glucans to Ascopyrones P and T in Pezizales and Tuberales", Phytochemistry, vol. 33, No. 1, pp. 41-45, 1993.

Tania Ahmad, "Studies on the Degradation of Some Pentoses and of 1,5-Anhydro-D-Fructose, The Product of the Starch-Degrading Enzyme α-1,4-Glucan Lyase", Phd Thesis, The Swedish University of Agricultural Sciences, Sweden, pp. 1-34, 1995.

Stefan Freimund et al., "Dimeric structures of 1,5-anhydro-D-fructose", Carbohydrate Research, 308, pp. 195-200, 1998.

* cited by examiner

*Primary Examiner*—Shaojia Anna Jiang
*Assistant Examiner*—Michael C Henry
(74) *Attorney, Agent, or Firm*—Wenderoth, Lind & Ponack, L.L.P.

(57) ABSTRACT

A method for producing ascopyrone P from 1,5-D-anhydrofructose efficiently is provided. The method produces ascopyrone P by heating a solution of 1,5-D-anhydrofructose at a pH of 10 or less and a temperature of 100° C. or higher.

7 Claims, 3 Drawing Sheets

2-Hydroxymethyl-5-hydroxy-2,3-dihydro-4H-pyran-4-one

Influence of pH Adjustment on Conversion rate of 1,5-AF to APP

EFFICIENT PRODUCTION METHOD OF ASCOPYRONE P

TECHNICAL FIELD

This invention relates to a method of producing ascopyrone P (2-hydroxymethyl-5-hydroxy-2,3-dihydro-4H-pyran-4-one) efficiently.

BACKGROUND ART

In 1978, it was reported for the first time that ascopyrone P (structural formula: FIG. 1) was produced by pyrolysis of cellulose (refer to Shafizadeh, F., et al., Carbohydr. Res. 67, 433-447 (1978)). Thereafter, its three-dimensional structure was analyzed and revealed by $^1$H-NMR, $^{13}$C-NMR and infrared spectroscopy (IR).

Ascopyrone P (hereinafter referred to as APP) has been reported to have an antioxidant activity, an antibacterial activity and an ability of preventing browning (refer to WO00/56838, WO02/26060 and WO02/26061). It is a substance with very high functionality for which expectation has been increasingly raised lately. Further, it has also been reported that fungi of certain types in nature produce ascopyrone P (refer to M.-A. Baute, phytochemistry, 33, 41-45 (1993)).

A number of reports have been made on a method of preparing APP. In the case of a method of preparing APP by pyrolysis of cellulose, the yield of APP is as low as only about 1.4% with respect to cellulose which is a raw material, and a very complicated separation process is required in subsequent purification, thereby making it unrealistic to use this method for industrial production. Further, it has been reported that a number of compounds are produced from 1,5-D-anhydrofructose (hereinafter referred to as 1,5-AF) in aqueous strong alkali solution and APP is one of intermediates produced in the production process of these compounds (refer to Ahmad, T., Phd Thesis, The Swedish University of Agricultural Sciences, Sweden (1995)). However, APP is an intermediate under this condition, and a method of terminating the reaction by APP and a method of preparing APP as a final product are not described.

Although it has also been reported that APP can be enzymtically synthesized by crude extract of Pezizales orders (e.g. *Picaria leiocarpa* and *Anthracobia melaloma*) and Tuberales orders (e.g. *Tuber melanosporum*) to act on 1,5-AF, this method has been used only for preparation in milligrams. This preparation method shows a low yield and low efficiency despite taking considerable time and effort. Therefore, it is not suited for industrial use.

Recently, as a production method of APP using enzyme, a method with specifically defined production conditions has been applied for patent (refer to WO03/038085, WO03/038107 and WO03/038084). However, this method requires a long time for an enzyme reaction and needs to spend time for production of enzyme.

Meanwhile, 1,5-AF is sugar that can be prepared by degradation α-1,4-glucan such as starch by α-1,4-glucan lyase and can be mass-produced at low cost. Use of this sugar as an antibacterial agent (refer to JP-A 2001-89377 (the term "JP-A" as used herein means an "unexamined published Japanese patent application")), an antioxidant (refer to JP-A 9-505988) and a colorant (refer to JP-A2002-27945) has already been proposed.

DISCLOSURE OF THE INVENTION

An object of the present invention is to provide an efficient production method of APP.

Other objects and advantages of the present invention will become apparent from the following description.

The present inventors have made intensive studies on 1,5-AF and APP. As a result, they have found that APP can be prepared easily by heating 1,5-AF at high temperatures for a given time and have completed the present invention based on the finding.

That is, according to the present invention, firstly, the above objects and advantages of the present invention are achieved by a method for producing APP, which comprises heating 1,5-AF at a pH of 10 or less and a temperature of 100° C. or higher.

Further, according to the present invention, secondly, the above objects and advantages of the present invention are achieved by a method for producing APP efficiently comprising heating 1,5-AF in the co-presence of an antioxidant.

According to the present invention, ascopyrone P can be produced more highly efficiently and at lower cost than conventional methods by heating a solution of 1,5-D-anhydrofructose at a pH of 10 or less.

Figure 1:
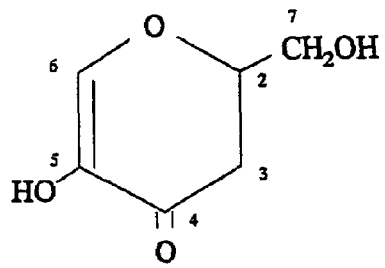
FIG. 1 is the structural formula of ascopyrone P (2-hydroxymethyl-5-hydroxy-2,3-dihydro-4H-pyran-4-one).

BEST MODE FOR CARRYING OUT THE INVENTION 1,5-AF used in the production method of the present invention can be prepared by, for example, reacting α-1,4-glucan lyase which has been extracted from red alga *Gracilaria verrucosa* and purified with starch or maltdextrin.

The thus prepared 1,5-AF containing solution can be further separated and purified to prepare a high-purity solution having a 1,5-AF content of, for example, not lower than 99%. Further, without particularly carrying out the separation and purification, the solution having a 1,5-AF content of, for example, 40% may be used as it is.

The relationship between heating conditions and a conversion rate of 1,5-AF to APP can be determined by determining the conversion rate of a solution obtained by heating the 1,5-AF solution.

The conversion rate of 1,5-AF to APP is calculated in the following manner.

A standard solution prepared by using APP dried under reduced pressure is subjected to high-performance liquid chromatography (HPLC) analysis under conditions shown in Table 1 to obtain a chromatogram. Based on the APP peak area in the obtained chromatogram, the amount of produced APP is calculated from the APP peak area in the HPLC chromatogram of a measurement sample (APP containing solution produced in accordance with the production method of the present invention). The conversion rate of 1,5-AF to APP is determined by calculating the wt % of the amount of the produced APP to the amount of 1,5-AF used in the heat treatment.

TABLE 1

| Column: Separation Mode | Ligand Exchange |
|---|---|
| Column Temperature | 30° C. |
| Flow Rate | 1.0 ml/min |
| Eluent | Distilled Water |
| Detector | Differential Refractometer |

In the APP production method of the present invention, the 1,5-AF solution is heated at a pH of 10 or less and a temperature of 100° C. or higher. Although APP is produced even at higher pH, a number of byproducts are produced, thereby making separation and purification of APP very difficult. A preferred condition is a pH of 2 to less than 7, and in consideration of the stability of APP, a more preferred condition is a pH of 2 to 4.

The heating condition in the APP production method of the present invention is preferably a temperature of 120° C. or higher, more preferably 140 to 250° C. Further, although varying depending on the heating temperature and the heating method, the heating time is 1 second to 24 hours at 100° C. or higher, for example, preferably 1 second to 5 hours at 120° C. or higher, more preferably about 1 second to 2 hours at 140 to 250° C.

As the heating method, various heating devices can be used. Illustrative examples of the heating devices include a pressurized steam sterilizer, a jet cooker, and an oil bath. Illustrative examples of heating media used in the heating devices include various oils, steam, and superheated steam.

Illustrative examples of a solvent to dissolve 1,5-AF include water and a mixture of water and a water-miscible organic solvent. Illustrative examples of the water-miscible organic solvent include a lower alcohol having 1 to 3 carbon atoms.

The concentration of 1,5-AF in the solvent may be 0.1 to 90 wt %, for example.

Further, the present inventors have found that APP tends to be stabilized in the co-presence of an antioxidant. Accordingly, APP can be produced more efficiently by adding other antioxidant to the 1,5-AF solution and heating the solution. Illustrative examples of the other antioxidant include ascorbic acid, erythorbic acid, ethylenediamine tetraacetic acid and theirs salts, tocopherol, butylhydroxyanisol, dibutylhydroxytoluene, and polyphenol. Of these, ascorbic acid, erythorbic acid, ethylenediamine tetraacetic acid and theirs salts are preferred.

Thus, separation and purification of APP from the APP containing solution obtained by the above method can be conducted by chromatography, for example. When APP powder obtained by freeze drying after separation and purification was analyzed by use of mass spectrometry based on an electron-impact ionization method, a molecular ion ($M^+$) was observed at m/z144. Further, when the same sample was dissolved in deuterium oxide and analyzed by use of $^1$H-NMR and $^{13}$C-NMR methods, the results shown in Table 2 were obtained. These values resulting from the mass spectrometry and NMR matched the corresponding already reported values of APP (refer to M.-A. Baute, phytochemistry, 33, 41-45 (1993)), and it was confirmed that the material produced by the method of the present invention had the structure shown in FIG. 1, whereby it was APP.

TABLE 2

| Attribution | $^{13}$C Shift (ppm) | $^1$H Shift (ppm) | Spin Coupling Constant J(Hz) |
|---|---|---|---|
| C-2 | 80.3 | 4.58 | |
| C-3 | 36.9 | 2.52, 2.88 | $J_{3,3} = 17.3$ |
| | | | $J_{2,3} = 15.1$ |
| | | | $J_{2,3} = 3.4$ |
| C-4 | 192.0 | — | |
| C-5 | 135.3 | — | |
| C-6 | 152.1 | 7.54 | |
| C-7 | 63.0 | 3.79, 3.89 | $J_{7,7} = 12.8, J_{2,7} = 5.6, 2.4$ |

Ascopyrone P obtained by the production method of the present invention can be used in a food industry, a drug industry, a chemical industry and the like. As a method of using ascopyrone P, it can be added to a food material or a food product, for example. Further, as another method, it is also possible to add 1,5-AF to a product and carry out the method of the present invention during the food manufacturing process. For example, in the food manufacturing process, heat treatment steps such as cooking and sterilization often exist. Thus ascopyrone P is produced in a food by adding 1,5-AF to a food material in advance and heating the material under the conditions of the present invention.

Hereinafter, the present invention will be further described by examples. However, the present invention shall not be limited by these examples in any way.

EXAMPLES

Example 1

Figure 2:
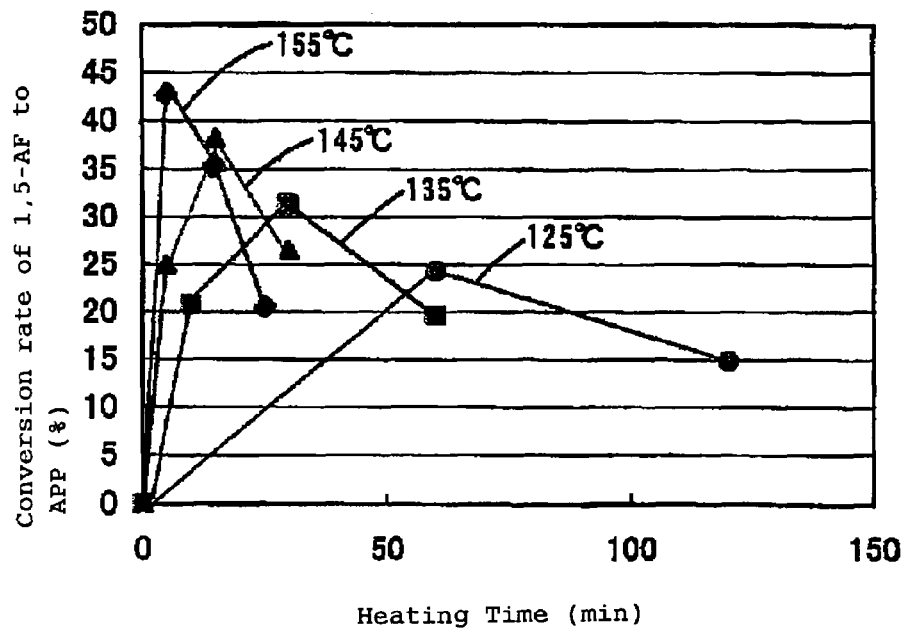
FIG. 2 is a diagram showing the relationships between heating times and a conversion rate of 1,5-AF to APP when a 1,5-AF aqueous solution was heated at 125° C., 135° C., 145° C. and 155° C.

1,5-AF (purity: 99%) was dissolved in water to prepare an aqueous solution having a concentration of 10%. The solution was heated at 125° C., 135° C., 145° C. and 155° C. by use of a pressurized heat sterilizer to examine the relationships between heating times and conversion rates of 1,5-AF to APP at these temperatures. As a result, as shown in FIG. 2, it was found that APP was produced from 1,5-AF under these heating conditions and that the highest yield was achieved at 155° C. in the heating temperature range from 125° C. to 155° C. Further, it was also found that excessive heating decomposed produced APP, resulting in a reduction in yield. From the above results, it was revealed that APP could be produced efficiently in a short time by heating 1,5-AF at a high temperature for a given time.

Example 2

Figure 3:
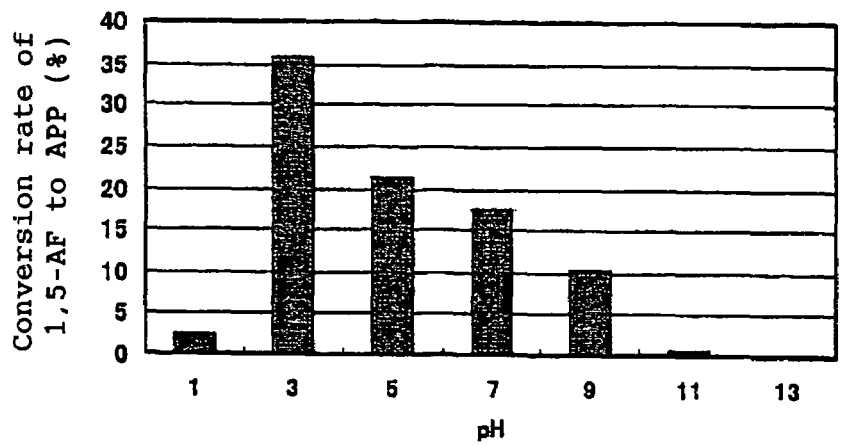
FIG. 3 is a diagram showing the results of comparisons of the conversion rate when a 1,5-AF aqueous solution was heat-treated after having its pH adjusted.

Samples resulting from adjusting 1,5-AF aqueous solutions having a concentration of 10% to a pH of 1 to 13 by pH regulators shown in the following Table 3 were heated in an autoclave at 121° C. for 30 minutes to examine the influence of pH on conversions of 1,5-AF to APP. The results are shown in FIG. 3.

TABLE 3

| pH | pH regulator |
|---|---|
| 1.0 | Hydrochloric Acid |
| 3.0 | Acetate Buffer |
| 5.0 | Acetate Buffer |
| 7.0 | Phosphate Buffer |
| 9.0 | Carbonate Buffer |
| 11.0 | Sodium Hydroxide Solution |
| 13.0 | Sodium Hydroxide Solution |

It was revealed from the test results that the pH condition greatly influenced production of APP and APP was produced efficiently under acidic conditions in particular.

Example 3

1,5-AF was heated in the co-presence of an antioxidant. When antioxidants were added, in the concentrations shown in Table 4, to 1,5-AF (purity: 99%) aqueous solutions having a concentration of 10% and the solutions were heated at 145° C. for 15 minutes by use of a pressurized heat sterilizer, higher conversion rate of 1,5-AF to APP were achieved with the antioxidants than with no antioxidant.

TABLE 4

| Test Section | Conversion rate of 1,5-AF to APP (%) |
|---|---|
| No Antioxidant Added (Only AF) | 38 |
| Ascorbic Acid 1% | 53 |
| EDTA-Na 0.1% | 42 |
| Ascorbic Acid 1% EDTA-Na 0.1% | 53 |

Example 4

1,5-AF aqueous solutions having a concentration of 10% which were adjusted to a pH of 3.0 by use of an acetate buffer were heated in an autoclave at 121° C. for 30 minutes and 60 minutes, and conversion rate of 1,5-AF to APP were checked. The results are shown in Table 5.

TABLE 5

| Heating Time (minutes) | Conversion rate of 1,5-AF to APP (%) |
|---|---|
| 30 | 36 |
| 60 | 45 |

Example 5

Figure 4:
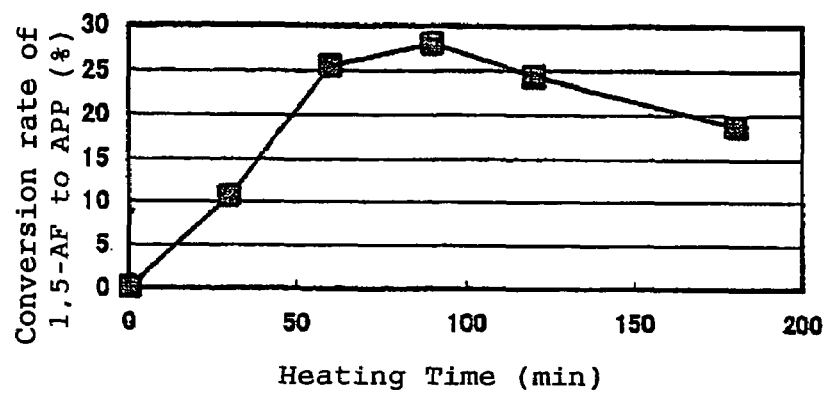
FIG. 4 is a diagram showing the relationship between heating time and a conversion rate of 1,5-AF to APP when a 1,5-AF aqueous solution (pH: 3.4) was heated at a temperature of 120° C.
Figure 5:
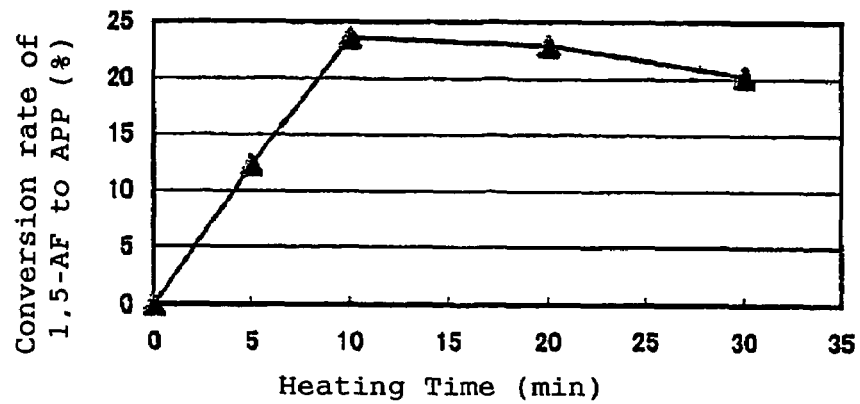
FIG. 5 is a diagram showing the relationship between heating time and a conversion rate of 1,5-AF to APP when a 1,5-AF aqueous solution (pH: 3.4) was heated at a temperature of 150° C.
Figure 6:
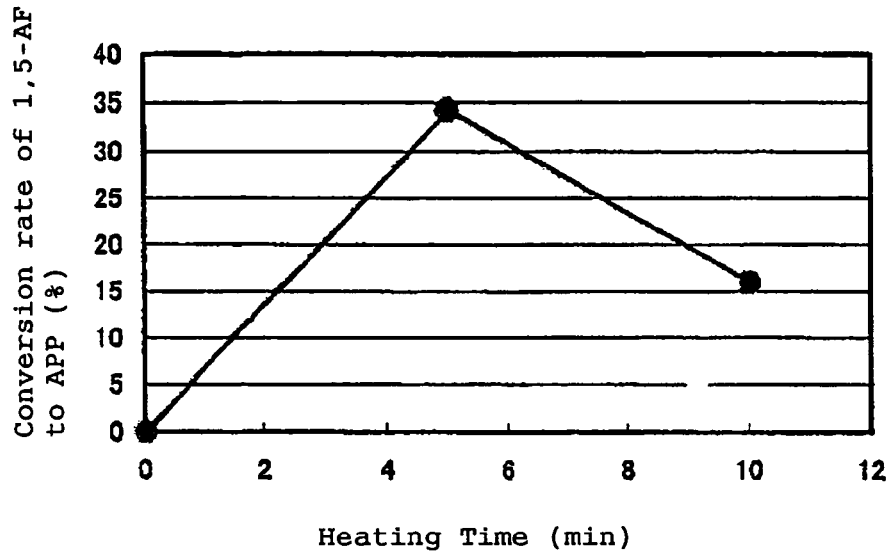
FIG. 6 is a diagram showing the relationship between heating time and a conversion rate of 1,5-AF to APP when a 1,5-AF aqueous solution (pH: 3.4) was heated at a temperature of 170° C.

1,5-AF solutions having a concentration of 10% which were adjusted to a pH of 3.4 by use of an acetate buffer were filled in stainless-steel pressure-resistant containers and heated in oil baths of 120° C., 150° C. and 170° C. for given times to check conversion rate of 1,5-AF to APP. The results are shown in FIGS. 4, 5 and 6. As indicated by the result shown in FIG. 6, about 35% of APP was produced by heating at 170° C. for 5 minutes. Further, there existed heating times suited for the heating temperatures, and the efficient heating conditions were revealed.

Example 6

1,5-AF solutions having a concentration of 30% which were adjusted to a pH of 3.0 by use of an acetate buffer were filled in stainless-steel pressure-resistant containers and heated in oil baths of 160° C., 180° C. and 200° C. for 3 minutes to prepare APP. The results are shown in FIG. 6.

TABLE 6

| Temperature | Conversion rate of 1,5-AF to APP (%) |
|---|---|
| 160° C. | 9.6 |
| 180° C. | 22.2 |
| 200° C. | 31.4 |

Example 7

Antioxidants were added, in the concentrations shown in Table 7, to 1,5-AF aqueous solutions having a concentration of 10% which were adjusted to a pH of 3.5 by use of an acetate buffer. The solutions were sealed in stainless-steel pressure-resistant containers and heated in an oil bath of 125° C. for 30 minutes to prepare APP. As a result, the test section containing ascorbic acid produced APP in an amount about twice as large as that produced by the test section containing no antioxidant.

TABLE 7

| Test Section | Conversion rate of 1,5-AF to APP (%) |
|---|---|
| No Antioxidant Added | 10.7 |
| Ascorbic Acid 1% | 21.3 |
| Chlorogenic Acid 1% | 13.9 |

Example 8

Figure 7:
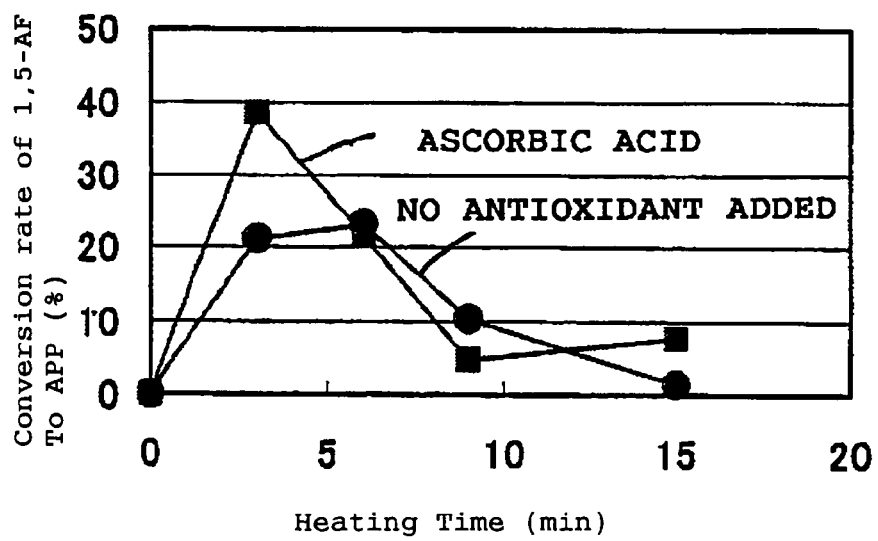
FIG. 7 is a diagram showing a conversion rate of 1,5-AF to APP when 1% of ascorbic acid was added to a 1,5-AF aqueous solution and the solution was then heated.

A 1,5-AF aqueous solution having a concentration of 10% and a 1,5-AF aqueous solution having a concentration of 10% to which 1% of ascorbic acid was added were filled in stainless-steel pressure-resistant containers and heated in an oil bath of 180° C. for 3 to 15 minutes. The conversion rate of 1,5-AF to APP at that time are shown in FIG. 7. When the solution containing ascorbic acid was heated for 3 minutes, about 40% of 1,5-AF was converted into APP, showing the highest yield.

Example 9

Curry was cooked by use of a commercial roux. 0.1% of 1,5-AF was added, and the curry was vacuum-packed and then sterilized by heating at 135° C. for 5 minutes. After cooling, the content of APP in the curry was measured. It was found that APP was contained in a proportion of 0.01% of the whole curry.

The invention claimed is:

1. A method for producing ascopyrone P, which comprises heating an aqueous solution of 1,5-D-anhydrofructose at a pH of 2 to less than 7 and a temperature of 100° C. or higher.
2. The method of claim 1, wherein the heating is conducted at a temperature of 120° C. or higher.
3. The method of claim 1, wherein the heating is conducted for 1 second to 24 hours.
4. The method of claim 1, wherein the pH is a pH of 2 to 4.
5. The method of claim 1, wherein the heating is conducted in the presence of an antioxidant.
6. The method of claim 5, wherein the antioxidant is at least one selected from the group consisting of ascorbic acid, erythorbic acid, ethylenediamine tetraacetic acid, and their salts.
7. The method of claim 1, wherein the pH is a pH of 4 to less than 7.

* * * * *